United States Patent [19]

Hampton et al.

[11] 4,207,885

[45] Jun. 17, 1980

[54] WOVEN ELASTIC COMPRESSION BANDAGE

[75] Inventors: Richard Hampton, Clemmons; P. Frank Hanes, Jr., Winston-Salem, both of N.C.

[73] Assignee: Carolon Company, Winston-Salem, N.C.

[21] Appl. No.: 18,147

[22] Filed: Mar. 7, 1979

[51] Int. Cl.$^2$ .................. A61L 15/00; D03D 23/00
[52] U.S. Cl. .............................. 128/156; 139/419; 139/422
[58] Field of Search .................. 128/155–156, 128/163–166.5, 169–170; 139/421–422, 419

[56] References Cited

U.S. PATENT DOCUMENTS

| 783,280 | 2/1905 | Jagers | 128/155 |
| 1,748,470 | 2/1930 | Domizlaff | 128/156 |
| 3,221,736 | 12/1965 | Heitzmann | 128/156 |

FOREIGN PATENT DOCUMENTS 1060729  3/1967  United Kingdom ............... 128/156

Primary Examiner—C. Fred Rosenbaum
Attorney, Agent, or Firm—Burns, Doane, Swecker & Mathis

[57] ABSTRACT

An elastic compression bandage of narrow woven fabric includes cotton weft yarn picks and textured stretch nylon multifilament warp yarns having total deniers in the range of from 210 to 560. The construction provides from 10 to 16 weft yarn picks per inch and from 30 to 40 warp yarns per inch in the as-woven fabric. Spaced apart across the width of the fabric are pairs of warp yarns interwoven with the weft yarn picks in a leno construction that provides high frictional resistance to slippage between those warp yarns and the weft yarns. The ratio of leno pairs to non-leno warp yarns is in the range of from 1/6 to 1/14. The non-leno warp yarns and the weft yarn picks are interwoven in a 1×1 weave. The leno pairs are in a pretensioned state when the bandage is in an unstretched condition.

7 Claims, 4 Drawing Figures

U.S. Patent
Jun. 17, 1980
4,207,885
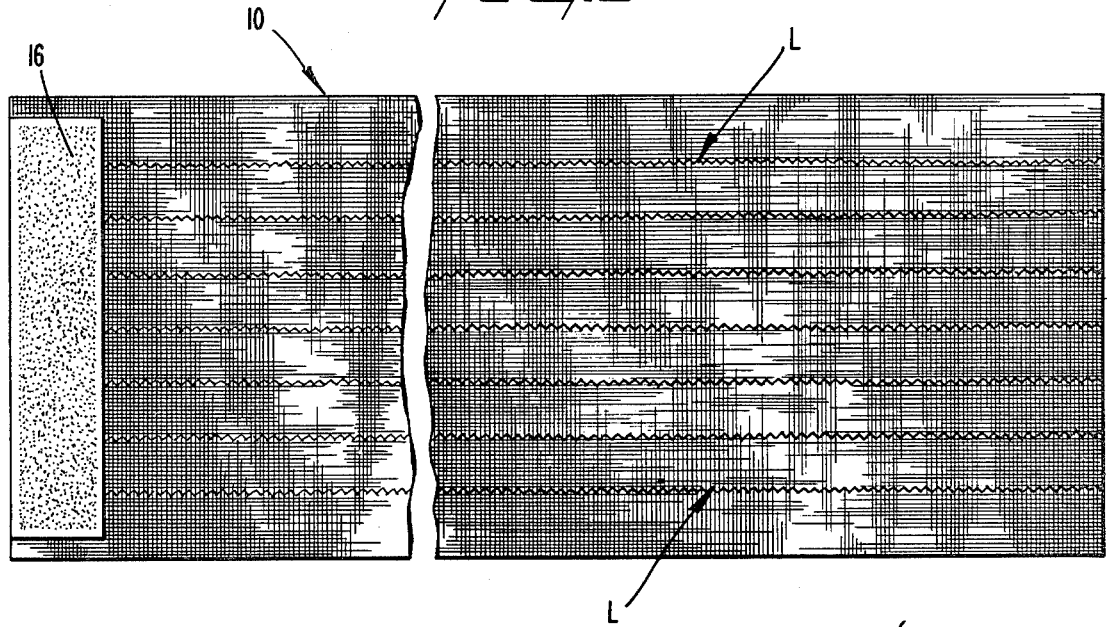
Fig.1
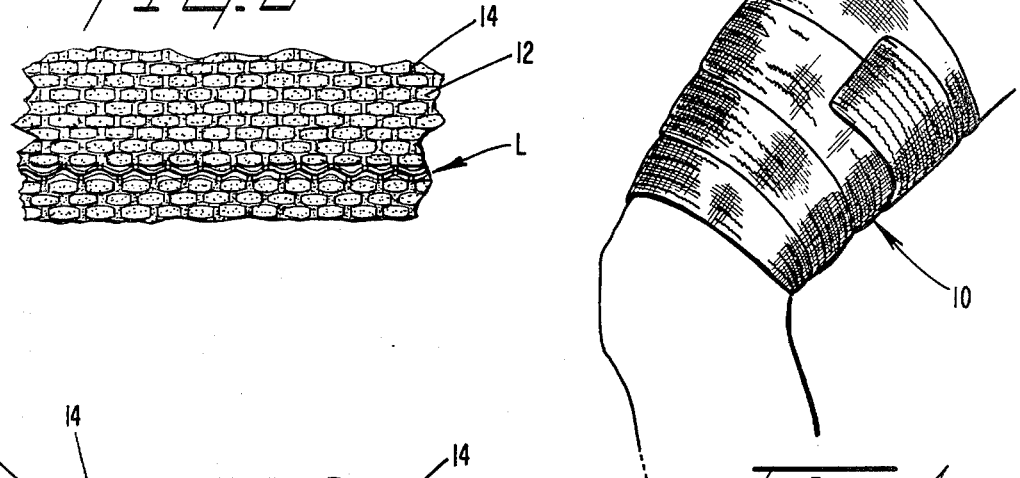
Fig.2
Fig.4
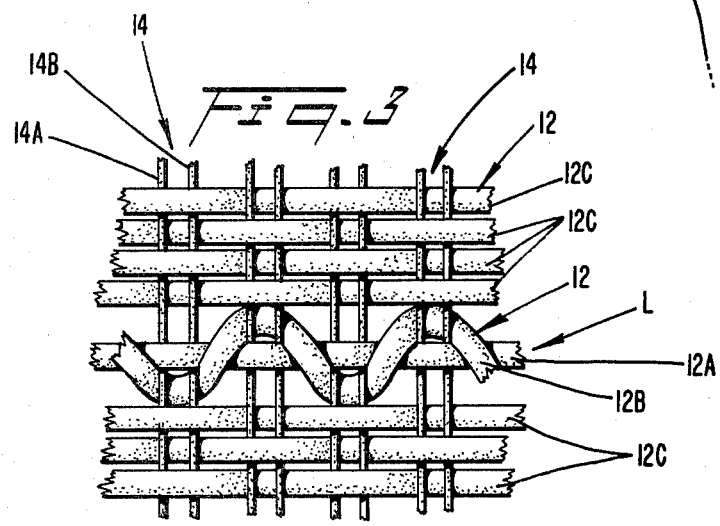
Fig.3

WOVEN ELASTIC COMPRESSION BANDAGE

BACKGROUND AND OBJECTS OF THE INVENTION

The present invention relates to woven elastic compression bandages of the type used for wrapping sprained ankles or for other applications where the stretched strip is wrapped around a part of the body.

Woven elastic compression bandages have long been used in the treatment of humans and animals. Such bandages are stretchable in a longitudinal direction to about twice their relaxed length and are applied by being wrapped in a stretched condition around that part of the patient's body being treated, i.e., appendage, trunk, etc.

Two general types of woven elastic compression bandages have been available. In one type, the contraction power was provided by warp yarns of elastomeric material, such as rubber, the "Spandex" material available from E. I. duPont de Nemours and Co., or the like. In the other type, the contraction power was provided by warps formed from "stretch" yarns of such materials as nylon. These latter yarns get their primary stretch characteristics from configurational aspects (e.g., crimps or the like) of the individual filaments which make up the multifilament yarn ends.

Woven elastic bandages relying upon elastomeric materials for their stretchability qualities typically have elastomeric warp yarns located at intervals across the width of the woven fabric, with inelastic warp yarns (e.g., cotton yarns) disposed in the zones between the elastomeric warp yarns. In one such construction the elastomeric warp yarns were interwoven with weft yarn picks in a 1×1 weave and the cotton warp yarns were interwoven with the weft yarn picks in a 2×2 weave.

These elastomeric yarn bandages have been used widely, but they are subject to various disadvantages. For example, their durability is not great, particularly in service conditions where washing is required, and the contraction forces developed in response to elongations of the bandages are not entirely satisfactory. Additional "snap back" capacity and greater uniformity of compression forces in use would enhance the desirability of these bandages, but such improvements do not appear to be likely.

Stretch nylon elastic compression bandages available prior to the present invention had many excellent qualities. In one such construction, textured multifilament nylon yarns made up the entire warp of the fabric, providing a multiplicity of sources of contraction power over the entire width of the fabric and providing exceptional tensile strength. Moreover, this construction retained its desirable qualities over a long period of use, even in the face of repeated washings in water hot enough to cause breakdown in elastomeric materials.

Nevertheless, there remained room for further improvement, even with respect to these stretch nylon bandages. Wrinkling or puckering of these fabrics sometimes occurred in connection with the application of the bandages to patients. Exact analysis of the underlying causes of such wrinkling or puckering is difficult if not impossible, but the phenomena appear to be associated with force patterns developed within the fabric during elongation of the bandage. As such elongation proceeds, the fabric tends to depart somewhat from its initially flat state and a rolling tendency sometimes is observed at the margins of the fabric. Additionally, it has been discovered that these fabrics are subject to some yarn slippage which is generally undesirable and which can detract significantly in some cases from the acceptability of the bandage product.

The present invention seeks to preserve the advantages of the stretch nylon elastic bandages while minimising or obviating problems of the type noted above.

It is another object of the invention to provide a novel elastic compression bandage and method for fabrication thereof.

It is a further object of the present invention to provide a novel elastic compression bandage which exerts enhanced compressive support upon a treated body area.

It is an additional object of the present invention to provide a novel elastic compression bandage which is highly resistant to width-wise warp yarn slippage.

It is yet another object of the present invention to provide a novel elastic compression bandage which minimizes the occurrence of wrinkling or puckering when the bandage is stretched.

SUMMARY OF THE INVENTION

An elastic compression bandage in accordance with the present invention has stretch nylon warp yarns located over substantially its entire width, but the warp yarns are not all interwoven in the same fashion with the weft yarn picks.

At locations spaced apart across the width of the fabric, pairs of warp yarns interlock with the weft yarn picks in a leno weave, wherein one warp yarn of each pair passes laterally over the other warp yarn of each pair between successive weft yarn picks. Such weaves are well known and they have long been used in open fabrics having spaces between the yarns. One warp yarn of each leno pair will pass over a weft yarn pick, laterally under the companion leno warp, over the next pick, and so on. The result is high friction relationship between the weft yarns and the leno warps, which relationship inhibits yarn to yarn slippage within the fabric.

In the zones between the spaced apart leno pairs, the bandage of the present invention has groups of 6 to 14 non-leno warp yarns. These non-leno warp yarns do not cross one another laterally of the fabric. They are interwoven with the weft yarn picks in a regular 1×1 weave. The weft yarn picks (preferably double strands of combed cotton 20s yarns) are present in the as-woven fabric at a density in the range of from 10 to 16 yarns per inch, while the warp yarns (preferably 6 ply, 70 denier, 17 filament, textured stretch nylon yarns) are present in the as-woven fabric at a density in the range of 30 to 40 yarns per inch of fabric width. The fabric is woven with the warp yarns under tension. Thereafter it is relaxed and subjected to conventional heat treatment to bulk and shrink the crimped filament nylon warp yarns so that the bandage will have its desired longitudinal stretchability (typically at least about 100%).

In a preferred form of the invention, the fabrication of the bandage is carried out in such a way that the leno warps in the fabric are at tension levels higher than the non-leno warps. This may be accomplished by supplying all the warp yarns from a single warp beam. Rotation of the beam will release equal amounts (mass rate) of all the yarns, but greater lengths of the leno warps are required to accomodate the lateral crossings of these yarns, so that extra extension of the leno warps will occur and these yarns will have a slightly pretensioned state in the fabric as compared with the non-leno warp yarns.

BRIEF DESCRIPTION OF THE DRAWINGS

These and other features and advantages of the invention will be understood more fully from a consideration of the following detailed description of a preferred embodiment illustrated in the accompanying drawings in which like numerals designate like elements and in which:

FIG. 1 is a plan view of a portion of an elastic compression bandage in accordance with the present invention, FIG. 2 is an enlarged view of a segment of the bandage of FIG. 1, FIG. 3 is a further enlarged, somewhat diagrammatic, view of a portion of the segment of FIG. 2, depicting the nature of a leno type interlocking of yarns, and FIG. 4 is a view of the bandage wrapped around the leg of a patient.

DETAILED DESCRIPTION OF A PREFERRED EMBODIMENT OF THE INVENTION

An elastic bandage 10 according to the present invention comprises a weave of warp yarns 12 and weft yarn picks 14. The weft yarn picks 14 each preferably comprise dual strands 14A, 14B of combed cotton yarn. In the British yarn number system, the size designations for cotton yarns of sizes suitable for use as the weft yarns in the fabric of this invention would range from 12s to 26s, with a yarn size of 20s being most preferred. A narrow loom appropriate for weaving the bandage fabric typically would include a weft yarn carrier element for carrying a loop of weft yarn across the fabric during the weaving operation, and the two legs of the loop would constitute the dual strands 14A and 14B of each weft yarn pick 14.

The warp yarns 12 each comprise 100% multifilament textured nylon, for example "6/70/17", i.e., a yarn having 6 ends of 70 denier, 17 filament nylon plied together to form one balanced yarn. Heavier or lighter warp yarn sizes may be employed depending upon the intended usage of the bandage. The total denier of each plied warp yarn is in the range of from 210 to 560, preferably 420.

In accordance with the present invention, selected pairs of the warp yarns are interwoven with the weft yarns by a known leno construction L, as diagrammatically depicted in FIG. 3, wherein a first yarn 12A of a leno pair extends over the weft yarn picks 14, and a second yarn 12B of the leno pair extends under the weft yarn picks 14 and crosses laterally over the first yarn 12A in the areas between picks. In order to illustrate these crossing relationships clearly in FIG. 3, it has been necessary to sacrifice accuracy in other respects, and this view should not be construed as indicative of actual size or space relationships. For example, the vertical space allotted in FIG. 3 to the leno warps 12A and 12B is exaggerated, and, although this view depicts the leno warp 12A as straight, the actual leno warps of each pair are both woven under tension so that neither is straight in the fabric.

Groups of non-leno warp yarns 12C are located in the spaces between the leno pairs and are preferably interwoven with the weft yarn picks 14 in a standard 1×1 plain weave. The use of the 1×1 weave in this construction is especially advantageous in that it assures that control will be maintained within the framework established by the preferred yarn densities and in the presence of the all-nylon warp.

The ratio of leno pairs to non-leno warp yarns is in the range of from 1/6 to 1/14 and is preferably 1/10, i.e., each leno pair is separated by 10 regular or non-leno warp yarns 12C. When fewer than about six plain, non-leno, warps 12C are used between leno pairs over the whole of the fabric, the resulting fabric has a "hard" feel that is not wholly desirable and the amount of hydrophillic cotton at the face of the bandage is not great enough to optimize user comfort. When more than about fourteen non-leno warps appear in the groups between leno pairs, the effectiveness of the leno pairs for maintaining fabric stability is significantly diminished.

During weaving of a bandage, the leno pairs 12A, 12B and the regular warp yarns 12C are supplied from a common warp beam on which all of the warp yarns have been wound under substantially the same tension. As the beam rotates to release the warp yarns to the weaving station, equal amounts (i.e., mass rates) of the leno yarns 12A, 12B and of the regular warp yarns 12C become available for incorporation under tension in the woven bandage. However, since the leno warp yarns must of necessity follow a more serpentine path than the non-leno yarns, due to the nature of the leno weave, the leno warp yarns must be extended more than the non-leno warp yarns, disposing the leno warp yarns in a prestressed condition in the bandage structure.

After the weaving operation, the bandage is heat-treated in a process which includes agitating the woven bandage fabric in a heat of about 180° F. for about 20 minutes. As a result of this heat treatment, the multifilament textured stretch nylon warp yarns 12A, 12B, and 12C will be bulked and shrunk to give the bandage the desired stretchability. One is able to obtain a 100% stretch in a longitudinal direction with a return to its original position when the tension is released.

The sizes and the densities in the fabric of the warp and weft yarns are of importance to the attainment of the best results. Cotton weft threads smaller than about No. 26s are apt to provide a fabric that is too open to constitute a desirable elastic compression bandage, while cotton weft yarns bigger than about No. 12s would be likely to interfere unduly with the required bulking of the fabric. Weft yarn densities in the fabric of greater than about 16 picks per inch of length of the as-woven fabric also would inhibit bulking of the fabric. Densities less than about 10 picks per inch will not weave satisfactorily under the normal conditions appropriate for the fabrication of the fabrics of the present invention. The sizes of the warp yarns provide the basic control over the overall weight of the fabric, which factor is fixed generally by the expectations of the users of the woven elastic compression bandages. The density in the fabric of the warp yarns affects a number of important factors. If fewer than about 30 warp yarns per inch of width of the as-woven fabric are used, the fabric is apt to have a gauzy appearance that offends the eye and is generally unsuitable in woven elastic compression bandages. Moreover, such open fabrics have a tendency to pinch the skin when they are used as elastic compression bandages. If more than about 40 warp yarns per inch are used, the nylon warp is apt to so dominate the face of the fabric that the beneficial qualities of the hydrophillic cotton weft yarns become ineffective as contributions to the bandage. About 35 warps per inch has been discovered to be particularly preferable, and this density of stretch nylon warp yarns provides a bandage of excellent contraction power.

Bulking of the fabric by the heat treatment develops a thin "blanket" of nylon filaments on both sides of the fabric. That "blanket" of nylon filaments establishes a large number of loops which can be made to serve as the "female" components of a "Velcro" type fastener or closure system for the wrapped-on bandage. A single strip 16 of the companion "Velcro" material, i.e., one with the "male" hook portions can then be applied to one end of the bandage roll as depicted in FIG. 1 and will adhere to the nylon loops on the side of the bandage fabric and thus provide a self-contained closure system. The need for other conventional types of closure means such as clips, pins or tie strings is thus eliminated.

It will be thus appreciated that the afore-described provision of leno weave construction in an elastic compression bandage achieves unique improvements in connection with the strength, durability and application ease of the bandage. The bandage has more spring-back power, resists width-wise warp slippage, and minimizes puckering tendencies during longitudinal stretching.

Although the invention has been described in connection with a preferred embodiment thereof, it will be appreciated by those skilled in the art that additions, modifications, substitutions, and deletions not specifically described may be made without departing from the spirit and scope of the invention as defined in the appended claims.

What is claimed is:

1. An elastic compression bandage extendable to a tensioned length at least about twice its relaxed length and being formed by a narrow woven fabric, the contraction power of said bandage being provided by textured stretch nylon warp yarns that are interwoven under tension with weft yarn picks and that are bulked and shrunk by treatment subsequent to such weaving, said fabric comprising:
   a plurality of weft yarn picks in the range of from about 10 to about 16 picks per inch of tensioned length of the as-woven fabric; and
   a plurality of warp yarns disposed across the entire width of the fabric with a density in the range of from about 30 to about 40 yarns per inch of width of the as-woven fabric, each warp yarn being stretchable and formed of textured stretch nylon, the total deniers of each warp being in the range of from about 210 to about 560;
   said plurality of warp yarns including spaced apart pairs of leno warps and groups of non-leno warps between said pairs of leno warps, with
   the ratio of leno pairs to non-leno warp yarns being in the range of from about 1/6 to 1/14 and
   the non-leno warp yarns and the weft yarn picks being interwoven in a 1×1 weave.

2. An elastic compression bandage according to claim 1, wherein each of said warp yarns is a ply yarn made up of a plurality of ends of 70 denier, 17 filament, yarn.

3. An elastic compression bandage according to claim 2, wherein each weft yarn pick is constituted by a double strand of cotton yarn of a size corresponding to yarn numbers in the range from 12s to 26s.

4. An elastic compression bandage according to claim 3, wherein
   said cotton weft yarns are of sizes corresponding approximately to the yarn number 20s,
   said weft yarn picks are present at a density of about 13.5 picks per inch of the as-woven fabric,
   said warp yarns are 6 ply yarns present in the as-woven fabric at a density of about 34 to 35 warp yarns per inch of the fabric width, and
   the number of non-leno warps in at least most of said groups located between pairs of leno warps is about 10.

5. An elastic compression bandage according to claim 4, further including a Velcro fastener mounted at one end of the bandage, and having hook portions projecting therefrom, said fastener being connectable with loops formed by filaments of said warp yarns to secure the bandage in place.

6. An elastic compression bandage extendable to a tensioned length at least about twice its relaxed length and being formed by a narrow woven fabric, the contraction power of said bandage being provided by textured stretch nylon warp yarns that are interwoven under tension with weft yarn picks and that are bulked and shrunk by treatment subsequent to such weaving, said fabric comprising:
   about 13 double strand picks per inch of 20s singles combed cotton weft yarn; and
   about 35 six ply, 70 denier, multifilament, textured stretch nylon yarns per inch across the width of the fabric;
   said plurality of warp yarns including spaced apart pairs of leno warps and groups of non-leno warps between said pairs of leno warps, with
   the ratio of leno pairs to non-leno warp yarns being in the range of from about 1/6 to about 1/14,
   the non-leno warp yarns and the weft yarn picks being interwoven in a 1×1 weave, and
   the leno warp yarns being in a pretensioned state in said fabric when said non-leno warp yarns are relaxed.

7. A method of making an elastic compression bandage of improved fabric stability, comprising
   providing a single warp beam on which textured stretch nylon yarns are wound at generally the same tension level, such yarns having a denier in the range of from 210 to 560 and being present on the beam in sufficient numbers that 30 to 40 warp yarns per inch of bandage width can be supplied from the beam to a weaving station,
   delivering the yarns from said beam at substantially equal mass rates by rotation of said beam, and
   manipulating said warp yarns and inserting weft yarn picks at said weaving station to provide (a) spaced apart leno warp pairs interlocked with said picks and (b) groups of 6 to 14 non-leno warps interwoven with said picks in a 1×1 weave in zones between leno pairs, whereby the lengths of said leno warp in the bandage are greater than the lengths of said non-leno warps, so that the tension level in the leno warps is higher than the tension level of the remaining warps.

* * * * *